United States Patent [19]
Bernstein et al.

[11] Patent Number: 5,837,221
[45] Date of Patent: *Nov. 17, 1998

[54] POLYMER-LIPID MICROENCAPSULATED GASES FOR USE AS IMAGING AGENTS

[75] Inventors: Howard Bernstein, Cambridge; Julie Ann Straub, Winchester; Henry T. Brush, Somerville; Charles C. Church, Arlington, all of Mass.

[73] Assignee: Acusphere, Inc., Cambridge, Mass.

[*] Notice: This patent issued on a continued prosecution application filed under 37 CFR 1.53(d), and is subject to the twenty year patent term provisions of 35 U.S.C. 154(a)(2).

[21] Appl. No.: 681,710
[22] Filed: Jul. 29, 1996
[51] Int. Cl.$^6$ .............................. A61K 49/04; A61K 9/14
[52] U.S. Cl. ............................ 424/9.52; 424/489
[58] Field of Search ................... 424/9.52, 9.51, 424/9.5, 450, 489, 497, 498, 502, 501, 499; 128/662.02; 428/402, 402.24; 427/213.3; 264/4, 4.7; 600/458

[56] References Cited

U.S. PATENT DOCUMENTS

| | | | |
|---|---|---|---|
| 3,044,942 | 7/1962 | Babtist | 194/47 |
| 4,265,251 | 5/1981 | Tickner | 128/660 |
| 4,276,885 | 7/1981 | Tickner et al. | 128/660 |
| 4,442,843 | 4/1984 | Rasor et al. | 128/660 |
| 4,466,442 | 8/1984 | Hillmann et al. | 128/653 |
| 4,533,254 | 8/1985 | Cook et al. | 366/176 |
| 4,544,545 | 10/1985 | Ryan et al. | 424/1.21 |
| 4,572,203 | 2/1986 | Feinstein | 128/661 |
| 4,637,905 | 1/1987 | Gardner | 264/4.3 |
| 4,657,756 | 4/1987 | Rasor et al. | 424/9 |
| 4,681,119 | 7/1987 | Rasor et al. | 128/660 |
| 4,684,479 | 8/1987 | D'Arrigo | 252/307 |
| 4,718,433 | 1/1988 | Feinstein | 128/660 |
| 4,757,128 | 7/1988 | Domb et al. | 528/271 |
| 4,767,610 | 8/1988 | Long | 424/5 |

(List continued on next page.)

FOREIGN PATENT DOCUMENTS

| | | |
|---|---|---|
| 76144/91 | 11/1991 | Australia . |
| 87105799 | 4/1988 | China ............ A61K 49/02 |
| 0077752A2 | 4/1983 | European Pat. Off. ....... A61K 49/00 |
| 0 092 918 A1 | 11/1983 | European Pat. Off. . |
| 0 166 596 | 1/1986 | European Pat. Off. . |
| 0231091A1 | 8/1987 | European Pat. Off. ....... A61K 49/00 |
| 0245019A2 | 11/1987 | European Pat. Off. ....... A61K 49/00 |
| 0 324 938 B1 | 6/1988 | European Pat. Off. . |
| 0 295 055 A1 | 12/1988 | European Pat. Off. . |
| 0307087A1 | 3/1989 | European Pat. Off. ....... A61K 31/02 |
| 0324938A1 | 7/1989 | European Pat. Off. ....... A61K 49/00 |
| 0327490A1 | 8/1989 | European Pat. Off. . |
| 0357163A1 | 3/1990 | European Pat. Off. . |
| 0359246A2 | 3/1990 | European Pat. Off. ....... A61K 49/00 |
| 0454044A2 | 10/1991 | European Pat. Off. ........ A61K 9/14 |
| 0 458 745 A1 | 11/1991 | European Pat. Off. . |
| 0458745A1 | 11/1991 | European Pat. Off. ....... A61K 49/00 |
| 0467031A2 | 1/1992 | European Pat. Off. ....... A61K 49/00 |

(List continued on next page.)

OTHER PUBLICATIONS

Ikada e tal., *Chem. Abstracts*, 125(10), abs. No. 123787 (Sep. 2, 1996).
Gardner et al., "A Survey of Intraocular Gas Use in North America", *Arch. Ophthalmol.* 106:1188–9 (1988).
Jacobs, "Intraocular gas measurement using A–scan Ultrasound", *Current Eye Research* 5(8):575–8 (1986).
Nomura et al., "US Contrast Enhancement of Hepatic Tumor with Helium Gas Microbubbles: a Preliminary Report", *Jpn J Med. Ultrasonics*, 18(5): 28 (1991).
Vygantas et al., "Octafluorocyclobutane and Other Gases for Vitreous Replacement", *Arch. Ophthalmol.*, 90:235–6 (1973).
Sehgel, et al., "Influence of Postprocessing Curves On Contrast–Echographic Imaging: Preliminary Studies", *J. Ultrasound Med.*, 14:735–740(1995).
Allen & Hansen, "Pharmacokinetics of Stealth Versus Conventional Liposomes: Effect of Dose", *Biochimica et Biophysics Acta* 1068, 133–141 (1991).
Allen, et al., "Liposomes Containing Synthetic Lipid Derivatives of Poly(ethylene glycol) Show Prolonged Circulation Half–Lives in Vivo", *Biochimica et Biophysics Acta*, 1066, 29–36 (1991).
American Heart Association, *Abstracts of the 58th Scientific Sessions*, Circulation 72: Oct. 1985, III–427.

(List continued on next page.)

*Primary Examiner*—Gary E. Hollinden
*Assistant Examiner*—Michael G. Hartley
*Attorney, Agent, or Firm*—Arnall Golden & Gregory, LLP

[57] ABSTRACT

It has been discovered that the incorporation of gases, especially fluorinated gases such as perfluorocarbons, into microparticles formed from the combination of a natural or synthetic polymer and lipid have significantly enhanced echogenicity as compared with microparticles not including the lipid. Compounds other than lipids which are hydrophobic and limit the penetration and/or uptake of water into the microparticles can also be incorporated into the microparticles to enhance echogenicity. In the preferred embodiment, the polymers are synthetic biodegradable polymers. The microparticles are manufactured with a diameter suitable for the targeted tissue to be imaged, for example, with a diameter of between 0.5 and 8 microns for intravascular administration, and a diameter of between 0.5 and 5 mm for oral administration for imaging of the gastrointestinal tract or other lumens. Preferred polymers are polyhydroxy acids such as polylactic acid-co-glycolic acid, most preferably conjugated to polyethylene glycol or other materials inhibiting uptake by the reticuloendothelial system (RES). The most preferred lipids are phospholipids, preferably dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine, dilignoceroylphatidylcholine (DLPC), incorporated at a ratio of between 0.01–30 (w lipid/w polymer), most preferably between 0.1–10 (w lipid/w polymer). Microparticles for imaging using other detectable agents can be similarly manufactured.

28 Claims, 1 Drawing Sheet

5,837,221
Page 2

U.S. PATENT DOCUMENTS

| | | | |
|---|---|---|---|
| 4,774,958 | 10/1988 | Feinstein | 424/9.52 |
| 4,789,724 | 12/1988 | Domb et al. | 528/176 |
| 4,832,941 | 5/1989 | Berwing et al. | 424/9 |
| 4,844,882 | 7/1989 | Widder et al. | 424/9 |
| 4,857,311 | 8/1989 | Domb et al. | 424/78 |
| 4,859,363 | 8/1989 | Davis et al. | 252/312 |
| 4,865,836 | 9/1989 | Long | 424/5 |
| 4,888,176 | 12/1989 | Langer et al. | 424/426 |
| 4,895,876 | 1/1990 | Schweighardt et al. | 514/47 |
| 4,900,540 | 2/1990 | Ryan et al. | 424/9 |
| 4,927,623 | 5/1990 | Long | 424/5 |
| 4,957,656 | 9/1990 | Cerny | 252/311 |
| 4,985,550 | 1/1991 | Charpoit et al. | 536/18.4 |
| 4,987,154 | 1/1991 | Long | 514/772 |
| 4,993,415 | 2/1991 | Long | 604/22 |
| 5,077,036 | 12/1991 | Long | 424/5 |
| 5,078,146 | 1/1992 | Sato | 128/661.08 |
| 5,080,885 | 1/1992 | Long | 424/5 |
| 5,088,499 | 2/1992 | Unger | 128/654 |
| 5,107,842 | 4/1992 | LevEne et al. | 128/662.02 |
| 5,114,703 | 5/1992 | Wolf et al. | 424/5 |
| 5,123,414 | 6/1992 | Unger | 424/9.51 |
| 5,137,928 | 8/1992 | Erbel et al. | 521/56 |
| 5,141,738 | 8/1992 | Rasor et al. | 424/2 |
| 5,145,684 | 9/1992 | Liversidge et al. | 424/489 |
| 5,147,631 | 9/1992 | Glajch et al. | 424/9.5 |
| 5,149,319 | 9/1992 | Unger | 424/9.37 |
| 5,155,215 | 10/1992 | Ramney | 534/16 |
| 5,171,755 | 12/1992 | Kakufman | 514/749 |
| 5,205,290 | 4/1993 | Unger | 128/653.4 |
| 5,209,720 | 5/1993 | Unger | 604/22 |
| 5,230,882 | 7/1993 | Unger | 424/9.51 |
| 5,260,496 | 11/1993 | Meinert et al. | 570/179 |
| 5,271,928 | 12/1993 | Schneider et al. | 424/9 |
| 5,271,961 | 12/1993 | Mathiowitz et al. | 427/213.31 |
| 5,281,408 | 1/1994 | Unger | 424/4 |
| 5,284,645 | 2/1994 | Long | 424/5 |
| 5,334,381 | 8/1994 | Unger | 424/9 |
| 5,344,393 | 9/1994 | Roth et al. | 424/469 |
| 5,352,435 | 10/1994 | Unger | 424/9 |
| 5,354,549 | 10/1994 | Klaveness et al. | 424/9.45 |
| 5,362,478 | 11/1994 | Desai et al. | 424/9 |
| 5,393,524 | 2/1995 | Quay | 424/9 |
| 5,409,688 | 4/1995 | Quay | 424/9 |
| 5,413,774 | 5/1995 | Schneider et al. | 424/9.51 |
| 5,456,900 | 10/1995 | Unger | 424/9.4 |
| 5,496,535 | 3/1996 | Kirkland | 424/9.37 |
| 5,498,421 | 3/1996 | Grinstaff et al. | 424/450 |
| 5,501,863 | 3/1996 | Rossling et al. | |
| 5,505,932 | 4/1996 | Grinstaff et al. | 424/9.3 |
| 5,508,021 | 4/1996 | Grinstaff et al. | 424/9.322 |
| 5,512,268 | 4/1996 | Grinstaff et al. | 424/9.322 |
| 5,518,709 | 5/1996 | Sutton et al. | 424/9.52 |
| 5,527,521 | 6/1996 | Unger | 424/93 |
| 5,529,766 | 6/1996 | Klaveness et al. | |
| 5,536,490 | 7/1996 | Klaveness | 424/9.52 |
| 5,542,935 | 8/1996 | Unger et al. | 128/662.02 |
| 5,547,656 | 8/1996 | Unger | 424/9.4 |
| 5,556,610 | 9/1996 | Yan et al. | 424/9.52 |
| 5,558,854 | 9/1996 | Quay | 424/9.52 |
| 5,558,856 | 9/1996 | Klaveness | 424/9.37 |
| 5,562,893 | 10/1996 | Lohrmann | 424/9.52 |
| 5,565,215 | 10/1996 | Gref et al. | |
| 5,567,413 | 10/1996 | Klaveness | 424/9.51 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,618,514 | 4/1997 | Schroder | 424/9.5 |
| 5,648,062 | 7/1997 | Klaveness et al. | 424/9.34 |
| 5,686,060 | 11/1997 | Schneider et al. | |
| 5,705,187 | 1/1998 | Unger | 424/450 |
| 5,711,933 | 1/1998 | Bichon et al. | 424/9.52 |

FOREIGN PATENT DOCUMENTS

| | | | |
|---|---|---|---|
| 0494615A1 | 7/1992 | European Pat. Off. | |
| 0502814A2 | 9/1992 | European Pat. Off. | G01R 33/28 |
| 0 520 888 A1 | 12/1992 | European Pat. Off. | |
| 0 520 889 A1 | 12/1992 | European Pat. Off. | |
| 0535387 | 4/1993 | European Pat. Off. | |
| 0 552 802 A2 | 7/1993 | European Pat. Off. | |
| 0554213A1 | 8/1993 | European Pat. Off. | A61K 49/00 |
| 410470 | 3/1925 | Germany | 120/5 |
| 3834705A1 | 4/1990 | Germany. | |
| 4127442A1 | 2/1993 | Germany. | |
| 19510690 | 9/1996 | Germany. | |
| 2196730 | 10/1982 | Japan. | |
| 59-067229 | 4/1984 | Japan | A61K 49/042 |
| 63-60943 | 3/1988 | Japan | A61K 49/00 |
| 57-177790 | 8/1990 | Japan | A61K 49/00 |
| 1641280A1 | 4/1991 | U.S.S.R. | A61B 8/00 |
| 1718798A1 | 3/1992 | U.S.S.R. | A61B 5/00 |
| WO80/02365 | 11/1980 | WIPO | A61B 10/00 |
| WO89/06978 | 8/1989 | WIPO | A61K 49/00 |
| WO89/10118 | 11/1989 | WIPO | A61K 31/02 |
| WO 90/01952 | 3/1990 | WIPO. | |
| WO90/07491 | 7/1990 | WIPO | C07C 233/88 |
| WO91/09629 | 7/1991 | WIPO | A61K 49/00 |
| WO91/12823 | 9/1991 | WIPO | A61K 49/00 |
| WO91/15244 | 10/1991 | WIPO | A61K 49/00 |
| WO91/18612 | 12/1991 | WIPO | A61K 31/70 |
| WO91/02560 | 2/1992 | WIPO. | |
| WO92/05806 | 4/1992 | WIPO | A61K 49/00 |
| WO92/08496 | 5/1992 | WIPO | A61K 49/00 |
| WO92/11873 | 7/1992 | WIPO | A61K 49/00 |
| WO92/15284 | 9/1992 | WIPO | A61K 9/127 |
| WO 92/17212 | 10/1992 | WIPO. | |
| WO 92/17514 | 10/1992 | WIPO. | |
| WO 92/18164 | 10/1992 | WIPO. | |
| WO92/17212 | 10/1992 | WIPO | A61K 49/00 |
| WO92/17213 | 10/1992 | WIPO | A61K 49/00 |
| WO92/18165 | 10/1992 | WIPO | A61K 49/00 |
| WO92/18169 | 10/1992 | WIPO | A61K 49/00 |
| WO 92/19272 | 11/1992 | WIPO. | |
| WO92/21382 | 12/1992 | WIPO | A61K 49/00 |
| WO92/22247 | 12/1992 | WIPO | A61B 8/00 |
| WO92/22298 | 12/1992 | WIPO | A61K 31/47 |
| WO93/00930 | 1/1993 | WIPO | A61K 49/00 |
| WO93/00933 | 1/1993 | WIPO | A61K 49/00 |
| WO93/01798 | 2/1993 | WIPO | A61K 9/00 |
| WO93/05819 | 4/1993 | WIPO. | |
| WO93/06869 | 4/1993 | WIPO | A61K 49/00 |
| WO93/07905 | 4/1993 | WIPO. | |
| WO93/10440 | 5/1993 | WIPO | G01N 24/08 |
| WO93/17718 | 9/1993 | WIPO | A61K 49/00 |
| WO93/25242 | 12/1993 | WIPO | A61K 49/00 |
| WO 94/02122 | 2/1994 | WIPO. | |
| WO94/09829 | 5/1994 | WIPO | A61K 49/00 |
| WO 94/16739 | 8/1994 | WIPO. | |
| WO94/19101 | 9/1994 | WIPO | B01J 13/00 |
| WO94/21301 | 9/1994 | WIPO | A61K 49/00 |
| WO94/21302 | 9/1994 | WIPO | A61K 49/00 |
| WO94/21303 | 9/1994 | WIPO | A61K 49/00 |
| WO94/28939 | 12/1994 | WIPO | A61K 49/00 |
| WO95/01187 | 1/1995 | WIPO | A61K 49/00 |
| WO 95/03357 | 2/1995 | WIPO. | |
| 9506518 | 3/1995 | WIPO | B01F 17/00 |
| WO 95/06518 | 3/1995 | WIPO. | |
| WO 95/23615 | 9/1995 | WIPO | A61K 49/00 |
| WO 95/24184 | 9/1995 | WIPO | A61K 9/127 |
| WO 95/32006 | 11/1995 | WIPO. | |
| WO 96/04018 | 2/1996 | WIPO | A61K 49/00 |
| WO 96/18420 | 6/1996 | WIPO. | |

| | | |
|---|---|---|
| WO 96/38181 | 12/1996 | WIPO .......................... A61K 49/00 |
| WO 96/40277 | 12/1996 | WIPO . |
| WO 97/22409 | 6/1997 | WIPO . |

OTHER PUBLICATIONS

Association of University Radiologists, Association of University Radiologists Proceedings of Annual Meeting, *Journal of Clinical and Laboratory Research Investigative Radiology* 17:4, Abstract 110 (1982).

Beck, et al., "A New Long–Acting Injectable Microcapsule System For The Administration of Progesterone", *Fertility and Sterility,* 31(5):545–551 (1979).

Benita, et al., "Characterization of Drug–Loaded Poly(d, l–lactide) Microsheres", *J. Pharmaceutical Sciences,* 73(12):1721–1724 (1984).

Bleecker, H., et al., "On the Application of Ultrasonic Contrast Agents for Blood Flowmetry and Assessment of Cardiac Perfusion", *Journal of Ultrasound in Medicine,* 9:461–471 (1990).

Bleecker, H., et al., "Ultrasonic Characterization of Albunex, A New Contrast Agent", *Journal Acoustical Society of America,* 87:1792–1797 (1990).

Burns, P.N., "Mezzi Di Contrasto Per Ecografia Nella Diagnostic Radiologic", *La Radiologic Medica–Radiol Med.,* 87(Supple, 1 al, n 5):71–82 (1994).

Carroll, et al., "Gelatin Encapsulated Nitrogen Microbubbles As Ultrasonic Contrast Agents", *Invest. Radiol.,* 15:260–266 (1980).

Carroll, et al.,"Ultrasonic Contrast Enhancement Of Tissue By Encapsulated Microbubbles[1]", *Radiology,* 143:747–750 (1982).

Davis, P. L., et al., "Echogenicity Cause By Stable Microbubbles In a Protein–Lipid Emulsion", *The Journal of Clinical Ultrasound,* 9:249–252, Jun. 1981.

De Jong, N., et al., "Absorption and Scatter of Encapsulated Gas Filled Microspheres: Theoretical Considerations and Some Measurements", *Ultrasonics,* 30:95–103 (1992).

DeJong and Cate, "New Ultrasound Contrast Agents and Technological Innovations," *Ultrasonic* 34(2–5):587–590 (1996).

Deng, et al., "Synthesis And Characterization Of Block Copolymers From D,L–Lactide And Poly(Ethylene Glycol) With Stannous Chloride", *J. Of Polymer Science: Part C: Polymer Letters,* 28:411–416 (1990).

Epstein, P. S., et al., "On The Stability of Gas Bubbles In Liquid–Gas Solutions", *Journal of Chemical Physics* 18:1505–1509, Nov. 1950.

Feinstein, et al., "Contrast Echocardiography During Coronary Arteriography in Humans: Perfusion and Anatomic Studies", *J. Am. Coll. Cardiol.,* 11:59–65 (1988).

Feinstein, Steven B., et al., "Safety and Efficacy Of A New Transpulmonary Ultrasound Contrast Agent: Initial Multicenter Clinical Results," *Journal of American College of Cardiology,* 16:316–324, Aug. 1990.

Feinstein, Steven B., et al., "Microcardial Contrast Echocardiography: Examination of Infracoronary Injections. Microbubble Diameters And Video Intensity Decay," *American Journal of Physilogic Imaging* 1:12–18 (1986).

Fobbe, V. F., "Farbkodierte Duplexsonographie Un Ultraschallkontrastmittel–Nachweis Von Renalen Perfusionsdefekten Im Tierexperiment", *Fortschr. Röntgenstr.* 154:242–245 (1991).

Fritzsch, et al., "SH U 508, A Transpulmonary Echocontrast Agent", *Invest. Radiol.,* 25(Suppl 1):160–161 (1990).

Fritzsch, et al., "Preclinical And Clinical Results With An Ultrasonic Agent", *Invest. Radiol.,* 23(Suppl 1):302–305(1988).

Handa, T., et al., "Phospholipid Monolayers at the Triolein–Saline Interface: Production of Microemulsion Particles and Conversion of Monolayers to Bilayers", *Biochemistry* 29:2884–2890 (1990).

Illum & Davis, "The Organ Uptake of Intravenously administered Colloidal Particles Can Be Altered Using A Non–Ionic Surfactant (Poloxamer 338)", *FEBS Lett.,* 167:79–82(1984).

Kabalnov, A. S., et al., "Safety and Efficacy of a New Transpulmonary Ultrasound Contrast Agent: Initial Multicenter Clinical Results", *Journal of Fluorine Chemistry* 50:271–284 (1990).

Keller, M. W., et al., "Successful Left Ventricular Opacification Following Peripheral Venous Injection of Sonicated Contrast Agent: An Experimental Evaluation", *American Heart Journal* :570–575, Sep. 1987.

Lasic, et al., "Sterically Stabilized Liposomes*: A Hypothesis On The Molecular Origin Of The Extended Circulation Times", *Biochimica et Biophysics Acta,* 1070:87–192(1991).

Long, David M., et al., "Experiments with Radiopaque Perflurocarbon Emulsions for Selective Opacification of Organs and total Body Angiography", *Investigative Radiology* 15:242–247 (1980).

Marshall, Nissim, *Encyclodedie Des Gaz, Encyclopedia of Gas* (1976).

Maruyama, et al., "Effect Of Molecular Weight In Amphipathic Polyethyleneglycol On Prolonging The Circulation Time Of Large Unilamellar Liposomes", *Chem. Pharm. Bull.,* 39(6):1620–1622(1991).

Mathiowitz, et al., "Morphology Of Polyanhydride Microsphere Delivery Systems", *J. Scanning Microscopy,* 4(2):329–340 (1990).

Mathiowitz, et al., "Novel Microcapsules For Delivery Systems", *Reactive Polymers,* 6:275–283(1987).

Mattrey, Robert F., et al., "Perfuorctylbromide: A Liver/ Spleen–Specific and Tumor–Imaging Ultrasound Contrast Material", *Radiology* 145:759–762, Dec. 1982.

Meltzer, R., et al., "Transmission of Ultrasonic Contrast Through the Lungs," *Ultrasound in Medicine and Biology,* 7(4):377–384 (1981).

Meltzer, et al., "Why do the Lungs Clear Ultrasonic Contrast?", *Ultrasound In Medicine & Biology,* 6:263–269 (1980).

Ohta, T., et al., "Effect of the Contrast Agent and the Agitation Method on the Size, Number and Stability of Microbubbles: A Basic Experiment for the Myocardial Contrast Study", *Japanese Journal of Medical Ultrasonics* 18:318–325 (1991).

Ophir, J., et al., "Contrast Agents In Diagnostic Ultrsound," *Ultrasound in Medicine and Biology* 15:319–333 (1989).

Parker, et al., "Attenuation of Ultrasound Magnitude and Frequency Dependence for Tissue Characterization", *Radiology,* 153(3):785–788(1984).

Parker & Wang, "Measurement of Ultrasonic Attenuation Within Regions selected from B–Scan Images", IEEE Trans. Biomed. *Enar. BME,* 30(8):431–437(1983).

Parker, et al., "A Particulate Contrast Agent with Potential for Ultrasound Imaging of Liver", *Ultrasound in Medicine & Biology,* 13(9):555–561(1987).

Rovai, et al., "Contrast Echo Washout Curves From The Left Ventricle: Application Of Basic Principles Of Indicator–Dilution Theory And Calculation Of Ejection Fraction", *J. Am. Coll. Cardiol.*, 10:125–134(1987).

Sato, et al., "Porous Biodegradable Microspheres for Controlled Drug Delivery. I. Assessment of Processing Conditions and Solvent Removal Techniques," *Pharmaceutical Research* 5(1):12–30 (1988).

Schlief, R., "Ultrasound Contrast Agents", *Current Opinion In Radiology* 3:198–207 (1991).

Schneider, et al., "Polymeric Microballoons As Ultrasound Contrast Agents Physical And Ultrasonic Properties Compared With Sonicated Albumin", *Invest. Radiol.*, 27:134–139(1992).

Schubert, K. V., et al., "Microemulsifying Fluorinated Oils With Mixtures of Fluorinated and Hydrogenated Surfactants, Colloids and Surfaces: Physicochemical and Engineering Aspects" 84:97–109 (1994).

Serratrice, G., et al., "Co–Colubilisation De Fluorocarbures Et D'Eau En Présence De Nouveaux Tensioactifs Non Ioniques Fluorés", *Journal Chim. Phys.* 87:1969–1980 (1990).

Shapiro, et al., "Intravenous Contrast Echocardiography With Use Of Sonicated Albumin In Humans: Systolic Disappearance Of Left Ventricular Contrast After Transpulmonary Transmission", *J. Am. Coll. Cardiol.*, 16:1603–1607(1990).

Smith, et al., "Left Heart Opacification With Peripheral Venous Injection Of A New Saccharide Echo Contrast Agent In Dogs", *J. Am. Coll. Cardiol.*, 13:1622–1628 (1989).

Swanson, D., et al., "Pharmaceuticals in medical Imaging, Radiopaque contrast Media, Radiopharmaceuticals, Enhancement Agents for Magnetic Resonance Imaging and Ultrasound," Ch. 22 pp. 682–685 (1990).

Szönyi, F., et al., "Syntheses De Tensioactifs F–Alkyles Non Ioniques Monodisperses", *Journal of Fluorine Chemistry* 36:195–209 (1987).

Torchilin, A. Klibanov, *Critical Reviews in Therapeutic Drug Carrier Systems,* 7(4):275–307(1991).

Verescon, Christian, et al., "An Easy, Convenient Was of Describing The Stability of Fluorocarbon Emulsions", *Journal de Chimie Physique* 86:2111–2116 (1989).

Violante, M. R., et al., "Particle Stabilized Bubbles For Enhanced Organ Ultrasound Imaging", *Investigative Radiology* 26:194–200, Nov. 1991.

Widder, Donald J., et al., "Microbubbles As a Contrast Agent for Neurosonography and Ultrasound–Guided Catheter Manipulation: In Vitro Studies", *AJR* 147:347–352, Aug. 1986.

Woodle, et al., "Versatility in Lipid Compositions Showing Prolonged Circulation With Sterically Stabilized Liposomes", *Biochimica et Biophysics Acta,* 1105:193–200(1992).

Yang, et al., "Computed Tomographic Liver Enhancement with Poly(d,l–Lactide)–Microencapsulated Contrast Media," *Investigative Radiology* 29:S267–S270 (1994).

Zarif, Leila, et al, "Synergistic Stabilization of Perfluorocarbon–Pluronic F–68 Emulsion by Perfluoroalkylated Polyhydroxylated Surgactants", *Jaocks* 66:10, Oct. 1989.

Ziskin, Marvin, C., et al., "Contrast Agents For Diagnostic Ultrasound", *Investigative Radiology* 6:500–505 (1972).

Zhu, et al., "Preparation, Characterization and Properties of Polylactide (PLA)–Poly(ethylene glyco) (PEG) Copolymers: A Potential Drug Carrier", *J. Polym. Sci., Polm. Lett. Ed.,* 24:331 (1986).

FIG. 1

POLYMER-LIPID MICROENCAPSULATED GASES FOR USE AS IMAGING AGENTS

BACKGROUND OF THE INVENTION

The present invention is generally in the area of diagnostic imaging agents, and is particularly directed to microparticulate ultrasound imaging contrast agents having lipid incorporated therein to maintain the echogenicity over time.

When using ultrasound to obtain an image of the internal organs and structures of a human or animal, ultrasound waves, waves of sound energy at a frequency above that discernable by the human ear, are reflected as they pass through the body. Different types of body tissue reflect the ultrasound waves differently and the reflections that are produced by the ultrasound waves reflecting off different internal structures are detected and converted electronically into a visual display.

For some medical conditions, obtaining a useful image of the organ or structure of interest is especially difficult because the details of the structure are not adequately discernible from the surrounding tissue in an ultrasound image produced by the reflection of ultrasound waves absent a contrast-enhancing agent. Detection and observation of certain physiological and pathological conditions may be substantially improved by enhancing the contrast in an ultrasound image by infusing an agent into an organ or other structure or interest. In other cases, detection of the movement of the contrast-enhancing agent itself is particularly important. For example, a distinct blood flow pattern that is known to result from particular cardiovascular abnormalities may only be discernible by infusing a contrasting agent into the bloodstream and observing the dynamics of the blood flow.

Materials that are useful as ultrasound contrast agents operate by having an effect on ultrasound waves as they pass through the body and are reflected to create the image from which a medical diagnosis is made. Different types of substances affect ultrasound waves in different ways and to varying degrees. Moreover, certain of the effects caused by contrast-enhancing agents are more readily measured and observed than others. In selecting an ideal composition for a contrast-enhancing agent, one would prefer the substance that has the most dramatic effect on the ultrasound wave as it passed through the body. Also, the effect on the ultrasound wave should be easily measured. There are three main contrast-enhancing effects which can be seen in an ultrasound image: backscatter, beam attenuation, and speed of sound differential.

BACKSCATTER: When an ultrasound wave that is passing through the body encounters a structure, such as an organ or other body tissue, the structure reflects a portion of the ultrasound wave. Different structures within the body reflect ultrasound energy in different ways and in varying strengths. This reflected energy is detected and used to generate an image of the structures through which the ultrasound wave has passed. The term "backscatter" refers to the phenomena in which ultrasound energy is scattered back towards the source by a substance with certain physical properties.

It has long been recognized that the contrast observed in an ultrasound image may be enhanced by the presence of substances known to cause a large amount of backscatter. When such a substance is administered to a distinct part of the body, the contrast between the ultrasound image of this part of the body and the surrounding tissues not containing the substance is enhanced. It is well understood that, due to their physical properties, different substances cause backscatter in varying degrees. Accordingly, the search for contrast-enhancing agents has focused on substances that are stable and non-toxic and that exhibit the maximum amount of backscatter.

The capability of a substance to cause backscatter of ultrasound energy depends on characteristics of the substance such as its ability to be compressed. When examining different substances, it is useful to compare one particular measure of the ability of a substance to cause backscatter known as the "scattering cross-section." The scattering cross-section of a particular substance is proportional to the radius of the scatterer, and also depends on the wavelength of the ultrasound energy and on other physical properties of the substance, J. Ophir and K. J. Parker, *Contrast Agents in Diagnostic Ultrasound*, Ultrasound in Medicine & Biology, vol. IS, n. 4, p. 319, 323 (1989).

In evaluating the utility of different substances as image contrasting agents, one can calculate which agents should have the higher scattering cross-section and, accordingly, which agents should provide the greatest contrast in an ultrasound image. It can be assumed that the compressibility of a solid particle is much less than that of the surrounding medium and that the density of the particle is much greater. Using this assumption, the scattering cross section of a solid particle contrast-enhancing agent has been estimated as 1.75 (Ophir and Parker, supra, at 325). For a pure liquid scatterer, the adiabatic compressibility and density of the scatterer and the surrounding medium are likely to be approximately equal, which would yield the result that liquids would have a scattering cross-section of zero. However, liquids may exhibit some backscatter if large volumes of a liquid agent are present. For example, if a liquid agent passes from a very small vessel to a very large one such that the liquid occupies substantially all of the vessel, the liquid may exhibit measurable backscatter. Nevertheless, it is appreciated by those skilled in the art that pure liquids are relatively inefficient scatterers compared to free gas microbubbles.

BEAM ATTENUATION: Another effect which can be observed from the presence of certain solid contrast-enhancing agents, is the attenuation of the ultrasound wave. Image contrast has been observed in conventional imaging due to localized attenuation differences between certain tissue types. K. J. Parker and R. C. Wang, "Measurement of Ultrasonic Attenuation Within Regions selected from B-Scan Images," *IEEE Trans. Biomed. Enar.* BME 30(8), p. 431–37 (1983); K. J. Parker, R. C. Wang, and R. M. Lerner, "Attenuation of Ultrasound Magnitude and Frequency Dependence for Tissue Characterization," Radiology, 153 (3), p. 785–88 (1984). It has been hypothesized that measurements of the attenuation of a region of tissue taken before and after infusion of an agent may yield an enhanced image. However, techniques based on attenuation contrast as a means to measure the contrast enhancement of a liquid agent are not well-developed and, even if fully developed, may suffer from limitations as to the internal organs or structures with which this technique can be used. For example, it is unlikely that a loss of attenuation due to liquid contrast agents could be observed in the image of the cardiovascular system because of the high volume of liquid contrast agent that would need to be present in a given vessel before a substantial difference in attenuation could be measured.

Absorption of energy by the particles occurs by a mechanism referred to as "relative motion." The change in attenuation caused by relative motion can be shown to increase linearly with particle concentration and as the square of the density difference between the particles and the surrounding medium. K. J. Parker, et al., "A Particulate Contrast Agent with Potential for Ultrasound Imaging of Liver," *Ultrasound in Medicine & Biology*, Vol. 13, No. 9, p. 555, 561 (1987). Therefore, where substantial accumulation of solid particles occurs, attenuation contrast may be a viable mechanism for observing image contrast enhancement although the effect is of much smaller magnitude than the backscatter phenomenon and would appear to be of little use in cardiovascular diagnoses.

SPEED OF SOUND DIFFERENTIAL: An additional technique to enhance contrast in an ultrasound image has been proposed based on the fact that the speed of sound varies depending on the media through which it travels. Therefore, if a large enough volume of an agent, through which the speed of sound is different than the surrounding tissue, can be infused into a target area, the difference in the speed of sound through the target area may be measurable.

In summary, diagnostic ultrasound is a powerful, non-invasive tool that can be used to obtain information on the internal organs of the body. The advent of grey scale imaging and color Doppler have greatly advanced the scope and resolution of the technique. Although techniques for carrying out diagnostic ultrasound have improved significantly, and for making and using contrast agents, there is still a need to enhance the resolution of the imaging for cardiac perfusion and cardiac chambers, solid organs, renal perfusion; solid organ perfusion; and Doppler signals of blood velocity and flow direction during real-time imaging.

A variety of natural and synthetic polymers have been used to encapsulate imaging contrast agents, such as air. Schneider et al., *Invest. Radiol.*, Vol. 27, pp. 134–139 (1992) describes three micron, air-filled polymeric particles. These particles were reported to be stable in plasma and under applied pressure. However, at 2.5 MHz, their echogenicity was low. Another type of microbubble suspension has been obtained from sonicated albumin. Feinstein et al., *J. Am. Coll. Cardiol.*, Vol. 11, pp. 59–65 (1988). Feinstein describes the preparation of microbubbles that are appropriately sized for transpulmonary passage with excellent stability in vitro. However, these microbubbles are short-lived in vivo, having a half life on the order of a few seconds (which is approximately equal to one circulation pass) because of their instability under pressure. Gottlieb, S. et al., *J. Am. Soc. Echo.*, Vol. 3, pp. 328 (1990), Abstract; and Shapiro, J. R. et al., *J. Am. Coll. Cardiol.*, Vol. 16, pp. 1603–1607 (1990). Gelatin-encapsulated air bubbles have been described by Carroll et al. (Carroll, B. A. et al., *Invest. Radiol*, Vol. 15, pp. 260–266 (1980), and Carroll, B. A. et al., *Radiology*, Vol. 143, pp. 747–750 (1982)), but due to their large sizes (12 and 80 $\mu$m) they would not be likely to pass through pulmonary capillaries. Gelatin-encapsulated microbubbles have also been described in PCT/US80/00502 by Rasor Associates, Inc. These are formed by "coalescing" the gelatin.

Microbubbles stabilized by microcrystals of galactose (SHU 454 and SHU 508) have also been reported by Fritzch et al. Fritzsch, T. et al., *Invest. Radiol.* Vol. 23 (Suppl 1), pp. 302–305 (1988); and Fritzsch, T. et al., *Invest. Radiol.*, Vol. 25 (Suppl 1), 160–161 (1990). The microbubbles last up to 15 minutes in vitro but less than 20 seconds in vivo. Rovai, D. et al., *J. Am. Coll. Cardiol.*, Vol. 10, pp. 125–134 (1987); and Smith, M. et al., *J. Am. Coll. Cardiol.*, Vol. 13, pp. 1622–1628 (1989). Gas microbubbles encapsulated within a shell of a fluorine-containing material is described in WO 96/04018 by Molecular Biosystems, Inc.

European Patent Application No. 90901933.5 by Schering Aktiengesellschaft discloses the preparation and use of microencapsulated gas or volatile liquids for ultrasound imaging, where the microcapsules are formed of synthetic polymers or polysaccharides. European Patent Application No. 91810366.4 by Sintetica S. A. (0 458 745 A1) discloses air or gas microballoons bounded by an interfacially deposited polymer membrane that can be dispersed in an aqueous carrier for injection into a host animal or for oral, rectal, or urethral administration, for therapeutic or diagnostic purposes. WO 92/18164 by Delta Biotechnology Limited describes the preparation of microparticles by spray drying under very controlled conditions as to temperature, rate of spraying, particle size, and drying conditions, of an aqueous protein solution to form hollow spheres having gas entrapped therein, for use in imaging. WO 93/25242 describes the synthesis of microparticles for ultrasonic imaging consisting of a gas contained within a shell of polycyanoacrylate or polyester. WO 92/21382 discloses the fabrication of microparticle contrast agents which include a covalently bonded matrix containing a gas, wherein the matrix is a carbohydrate. U.S. Pat. Nos. 5,334,381, 5,123, 414 and 5,352,435 to Unger describe liposomes for use as ultrasound contrast agents, which include gases, gas precursors, such as a pH activated or photo-activated gaseous precursor, as well as other liquid or solid contrast enhancing agents.

U.S. Pat. No. 5,393,524 to Quay discloses the use of agents, including fluorocarbons, for enhancing the contrast in an ultrasound image. The agents consist of extremely small bubbles, or microbubbles, of selected gases, which exhibit long life spans in solution and are small enough to traverse the lungs, enabling their use in ultrasound imaging of the cardiovascular system and other vital organs. WO095/ 23615 by Nycomed discloses microcapsules for imaging which are formed by coacervation of a solution, for example, a protein solution, containing a perfluorocarbon. PCT/US94/08416 by Massachusetts Institute of Technology discloses microparticles formed of polyethylene glycol-poly (lactide-co-glycolide) block polymers having imaging agents encapsulated therein, including gases such as air and perfluorocarbons. As described in WO094/16739 by Sonus Pharmaceuticals, Inc., while solids and liquids reflect sound to a similar degree, gases are known to be more efficient and are the preferred media for use as ultrasound contrast agents. In fact, as shown by example 12 of the Sonus PCT application, protein microcapsules were dismissed as raising safety concerns (as well as efficacy issues) when administered to mini-pigs, as compared to emulsions or colloidal suspensions.

None of these describe microparticles which can be detected using other methods for detection, such as x-ray, positron or photon emission tomography, or magnetic resonance imaging.

In all of these cases it is desirable to enhance the echogenicity of the imaging agent, in conjunction with enhancing or maintaining the stability and ease of manufacturing of the imaging agent. One way in which to increase the echogenicity of a microparticle is to increase the time encapsulated gases remain in the circulating microparticles. Unfortunately, in most cases, the gases diffuse out rapidly, regardless of the nature of the gas or the encapsulating material, particularly in the aqueous environment of the vascular circulation.

It is therefore an object of the present invention to provide microparticles with significantly enhanced echogenicity. It is another object of the invention to provide microparticles containing an imaging agent that can persist for more than a few circulation times in vivo. It is a further object of the present invention to provide microparticles which retain encapsulated gas for longer periods of time, therefore increasing the in vivo echogenicity of the microparticles.

It is another object of the invention to provide microparticles which contain an imaging agent. It is a further object of the invention to provide microparticles containing imaging agents that are targeted to specific regions of the body. It is still another object of the present invention to provide methods for making microparticles having imaging agents entrapped therein.

SUMMARY OF THE INVENTION

It has been discovered that the incorporation of gases, especially fluorinated gases such as perfluorocarbons, into microparticles formed from the combination of a natural or synthetic polymer and lipid have significantly enhanced echogenicity as compared with microparticles not including the lipid. Compounds other than lipids which are hydrophobic and limit the diffusion of water into the microparticles can also be incorporated into the microparticles to enhance echogenicity. In the preferred embodiment, the polymers are synthetic biodegradable polymers. The microparticles are manufactured with a diameter suitable for the targeted tissue to be imaged, for example, with a diameter of between 0.5 and 8 microns for intravascular administration, and a diameter of between 0.5 and 5 mm for oral administration for imaging of the gastrointestinal tract or other lumens. Preferred polymers are polyhydroxy acids such as polylactic acid-co-glycolic acid, polylactide or polyglycolide, most preferably conjugated to polyethylene glycol or other materials inhibiting uptake by the reticuloendothelial system (RES). The most preferred lipids are phospholipids, preferably dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), diligngoceroylphatidylcholine (DLPC), incorporated at a ratio of between 0.01–30 (w lipid/w polymer), most preferably between 0.1–10 (w lipid/w polymer).

Adhesion of these microparticles can be enhanced or reduced through the selection of bioadhesive polymers. For example, adhesion can be enhanced in the case where the polymer is used for oral administration. Targeting can also be achieved by selection of the polymer or incorporation within or coupling to the polymer of ligands which specifically bind to particular tissue types or cell surface molecules. Additionally, ligands may be attached to the microspheres which effect the charge, lipophilicity or hydrophilicity of the particle. The polymeric microparticles are useful in a variety of diagnostic imaging procedures including ultrasound imaging, magnetic resonance imaging, fluoroscopy, x-ray, and computerized tomography. The microspheres may be used in a variety of imaging applications including cardiology applications, blood perfusion applications as well as for organ and peripheral vein imaging.

DETAILED DESCRIPTION OF THE INVENTION

Methods are provided for the synthesis of polymeric delivery systems consisting of polymer-lipid microparticles which contain gases, especially perfluorocarbons. The microparticles are useful in a variety of diagnostic ultrasound imaging applications, particularly in ultrasound procedures such as blood vessel imaging and echocardiography. The incorporation of additional lipid significantly increases the echogenicity as compared with the same polymeric microparticles without the additional lipid.

Processes and Reagents for Making Microparticles

As used herein, the term microparticle includes microspheres and microcapsules, as well as microparticles, unless otherwise specified. Microparticles may or may not be spherical in shape. Microcapsules are defined as microparticles having an outer polymer shell surrounding a core of another material, in this case, a gas. Microspheres are generally solid polymeric spheres, which can include a honeycombed structure formed by pores through the polymer which are filled with a gas for imaging purposes, as described below.

Polymers

Both non-biodegradable and biodegradable matrices can be used mixed with lipids for delivery of gases, although biodegradable matrices are preferred, particularly for intravenous injection. Non-erodible polymers may be used for oral administration. Synthetic polymers are preferred due to more reproducible synthesis and degradation. The polymer is selected based on the time required for in vivo stability, i.e., that time required for distribution to the site where imaging is desired, and the time required for imaging. In one embodiment, microparticles with an in vivo stability of between about 20 to 30 minutes or more may be fabricated, for example for use in applications such as echocardiography, neurosonography, hysterosalpingography, and diagnostic procedures on solid organs. The in vivo stability of the contrast agent-encapsulated microparticles can be adjusted during the production by using polymers such as polylactide co glycolide copolymerized with polyethylene glycol (PEG). PEG if exposed on the external surface may elongate the time these materials circulate since it is hydrophilic.

Representative synthetic polymers are: poly(hydroxy acids) such as poly(lactic acid), poly(glycolic acid), and poly(lactic acid-co-glycolic acid), polyglycolides, polylactides, polylactide co-glycolide copolymers and blends, polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred non-biodegradable polymers include ethylene vinyl acetate, poly(meth)acrylic acid, polyamides, copolymers and mixtures thereof.

Examples of preferred biodegradable polymers include polymers of hydroxy acids such as lactic acid and glycolic acid, polylactide, polyglycolide, polylactide-co-glycolide, and copolymers with PEG, polyanhydrides, poly(ortho) esters, polyurethanes, poly(butyric acid), poly(valeric acid), poly(lactide-co-caprolactone), blends and copolymers thereof.

Examples of preferred natural polymers include proteins such as albumin and prolamines, for example, zein, and polysaccharides such as alginate, cellulose and polyhydroxyalkanoates, for example, polyhydroxybutyrate.

Bioadhesive polymers of particular interest for use in imaging of mucosal surfaces, as in the gastrointestinal tract, include polyanhydrides, polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Solvents

As defined herein, the polymer solvent is an organic solvent that is volatile or has a relatively low boiling point or can be removed under vacuum and which is acceptable for administration to humans in trace amounts, such as methylene chloride. Other solvents, such as ethyl acetate, ethanol, methanol, dimethyl formamide (DMF), acetone, acetonitrile, tetrahydrofuran (THF), acetic acid, dimethyle sulfoxide (DMSO) and chloroform also may be utilized, or combinations thereof. In general, the polymer is dissolved in the solvent to form a polymer solution having a concentration of between 0.1 and 60% weight to volume (w/v), more preferably between 0.25 and 30%.

Hydrophobic Compounds

Lipids

In general, incorporation of compounds which are hydrophobic and, in an effective amount, thereby limit penetration and/or uptake of water by the microparticles are effective in increasing echogenicity of polymeric microparticles having gas encapsulated therein, especially fluorinated gases such as perfluorocarbons. Lipids which may be used to stabilize gas inside the polymeric microparticles include but are not limited to the following classes of lipids: fatty acids and derivatives, mono-, di and triglycerides, phospholipids, sphingolipids, cholesterol and steroid derivatives, terpenes and vitamins. Fatty acids and derivatives thereof may include but are not limited to saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that may be used include, but are not limited to, molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauric, physeteric, myristoleic, palmitoleic, petroselinic, and oleic acids. Examples of branched fatty acids that may be used include, but are not limited to, isolauric, isomyristic, isopalmitic, and isostearic acids and isoprenoids. Fatty acid derivatives include 12-(((7'-diethylaminocoumarin-3-yl)carbonyl)methylamino)-octadecanoic acid; N-[12((7'diethylaminocoumarin-3-yl) carbonyl)methyl-amino) octadecanoyl]-2-aminopalmitic acid, N succinyl-dioleoylphosphatidylethanol amine and palmitoyl-homocysteine; and/or combinations thereof. Mono, di and triglycerides or derivatives thereof that may be used include, but are not limited to molecules that have fatty acids or mixtures of fatty acids between 6 and 24 carbon atoms, digalactosyldiglyceride, 1,2-dioleoyl-sn-glycerol;1,2-cdipalmitoyl-sn-3 succinylglycerol; and 1,3-dipalmitoyl-2-succinylglycerol.

Phospholipids which may be used include but are not limited to phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and $\beta$-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

Sphingolipids which may be used include ceramides, sphingomyelins, cerebrosides, gangliosides, sulfatides and lysosulfatides. Examples of Sphinglolipids include, but are not limited to, the gangliosides GM1 and GM2.

Steroids which may be used include but are not limited to cholesterol, cholesterol sulfate, cholesterol hemisuccinate, 6-(5-cholesterol 3$\beta$-yloxy) hexyl-6-amino-6-deoxy-1-thio-$\alpha$-D-galactopyranoside, 6-(5-cholesten-3 $\beta$-tloxy)hexyl-6-amino-6-deoxyl-1-thio-$\alpha$-D mannopyranoside and cholesteryl)4'-trimethyl 35 ammonio)butanoate.

Additional lipid compounds which may be used include tocopherol and derivatives, and oils and derivatized oils such as stearlyamine.

A variety of cationic lipids such as DOTMA, N-[1-(2,3-dioleoyloxy)propyl-N,N,N-trimethylammonium chloride; DOTAP, 1,2-dioleoyloxy-3-(trimethylammonio) propane; and DOTB, 1,2-dioleoyl-3-(4'-trimethyl-ammonio) butanoyl-sn glycerol may be used.

The most preferred lipids are phospholipids, preferably DPPC, DDSPC, DAPC, DSPC, DTPC, DBPC, DLPC and most preferably DPPC, DAPC and DBPC.

The lipid content ranges from .0.01–30 (w lipid/w polymer); most preferrably between 0.1–10 (w lipid/w polymer).

Other Hydrophobic Compounds

Other preferred hydrophobic compounds include amino acids such as tryptophane, tyrosine, isoleucine, leucine, and valine, aromatic compounds such as an alkyl paraben, for example, methyl paraben, and benzoic acid.

Imaging Agents

Gases

Any biocompatible or pharmacologically acceptable gas can be incorporated into the microparticles. The term gas refers to any compound which is a gas or capable of forming a gas at the temperature at which imaging is being performed. The gas may be composed of a single compound such as oxygen, nitrogen, xenon, argon, nitrogen or a mixture of compounds such as air. Fluorinated gases are preferred. Examples of fluorinated gases include $CF_4$, $C_2F_6$, $C_3F_8$, $C_4F_8$, $C_4F_{10}$, $SF_6$, $C_2F_4$, and $C_3F_6$. Perfluoropropane is particularly preferred because it provides an insoluble gas that will not condense at the temperature of use and is pharmacologically acceptable.

Other Imaging Agents

Other imaging agents can be incorporated in place of a gas, or in combination with the gas. Imaging agents which may be utilized include commercially available agents used in positron emission tomography (PET), computer assisted tomography (CAT), single photon emission computerized tomography, x-ray, fluoroscopy, and magnetic resonance imaging (MRI). Microparticless loaded with these agents can be detected using standard techniques available in the art and commercially available equipment.

Examples of suitable materials for use as contrast agents in MRI include the gatalinium chelates currently available, such as diethylene triamine pentacetic acid (DTPA) and gatopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte. Other useful materials include barium for oral use.

Microparticles and Methods for Manufacture Thereof

In the most preferred embodiment, the microparticles are produced by spray drying. Other techniques can be used, such as solvent extraction, hot melt encapsulation, and solvent evaporation, as discussed below. A major criteria is that the polymer must be dissolved or melted with the lipid, prior to forming the microparticle. Although described specifically with reference to incorporation of a lipid, it is understood that other useful hydrophobic compounds could be substituted for the lipid.

In a preferred embodiment, the gas is then replaced by applying a stream of the desired gas to, or pulling a vacuum on, the microparticles to remove the encapsulated gas, then filling with the desired gas.

a. Solvent Evaporation. In this method the polymer and lipid are dissolved in a volatile organic solvent such as methylene chloride. A pore forming agent as a solid or in solution may be added to the solution, for use in forming microparticles which are to incorporate gas as the imaging agent. If other imaging agents are to be incorporated, the imaging agent can be added as either a solid or in solution to the polymer solution. The mixture is sonicated or homogenised and the resulting dispersion or emulsion is added to an aqueous solution that contains a surface active agent such as TWEEN™ 20, TWEEN™ 80, PEG or poly (vinyl alcohol) and homogenised to form an emulsion. The resulting emulsion is stirred until most of the organic solvent evaporates, leaving microparticles. Several different polymer concentrations can be used (0.05–0.60 g/ml). Microparticles with different sizes (1–1000 microns) and morphologies can be obtained by this method. This method is useful for relatively stable polymers like polyesters.

Solvent evaporation is described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984), the teachings of which are incorporated herein.

However, labile polymers, such as polyanhydrides, may degrade during the fabrication process due to the presence of water. For these polymers, the following two methods, which are performed in completely organic solvents, are more useful.

b. Hot Melt Microencapsulation. In this method, the polymer and lipid are first melted and then mixed with the solid particles of the pore forming agent or solid or liquid diagnostic agent. The mixture is suspended in a non-miscible solvent (like silicon oil), and, while stirring continuously, heated to 5° C. above the melting point of the polymer. Once the emulsion is stabilized, it is cooled until the polymer particles solidify. The resulting microparticles are washed by decantation with a polymer non-solvent such as petroleum ether to give a free-flowing powder. Microparticles with sizes between one to 1000 microns can be obtained with this method. The external surfaces of particles prepared with this technique are usually smooth and dense. This procedure is used to prepare microparticles made of polyesters and polyanhydrides. However, this method is limited to polymers with molecular weights between 1000–50,000.

Hot-melt microencapsulation is described by E. Mathiowitz, et al., *Reactive Polymers*, 6, 275 (1987), the teachings of which are incorporated herein. Polyanhydrides, for example, made of bis-carboxyphenoxypropane and sebacic acid with molar ratio of 20:80 (P(CPP-SA) 20:80) (Mw 20,000), can be prepared by hot-melt microencapsulation or for example, poly(fumaric-co-sebacic) (20:80) (Mw 15,000) microparticles, can be prepared by hot-melt microencapsulation.

c. Solvent Removal. This technique was primarily designed for polyanhydrides. In this method, the pore forming agent is dispersed or dissolved in a solution of the selected polymer and lipid in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. The external morphology of particles produced with this technique is highly dependent on the type of polymer used.

d. Spray Drying of Microparticles. Microparticles can be produced by spray drying by dissolving a biocompatible polymer and lipid in an appropriate solvent, dispersing a pore forming agent into the polymer solution, and then spray drying the polymer solution, to form microparticles. As defined herein, the process of "spray drying" a solution of a polymer and a pore forming agent refers to a process wherein the solution is atomized to form a fine mist and dried by direct contact with hot carrier gases. Using spray drying apparatus available in the art, the polymer solution may be delivered through the inlet port of the spray drier, passed through a tube within the drier and then atomized through the outlet port. The temperature may be varied depending on the gas or polymer used. The temperature of the inlet and outlet ports can be controlled to produce the desired products.

The size of the particulates of polymer solution is a function of the nozzle used to spray the polymer solution, nozzle pressure, the flow rate, the polymer used, the polymer concentration, the type of solvent and the temperature of spraying (both inlet and outlet temperature) and the molecular weight. Generally, the higher the molecular weight, the larger the particle size, assuming the concentration is the same. Typical process parameters for spray drying are as follows: polymer concentration=0.005–0.20 g/ml, inlet temperature=30°–1000° C., outlet temperature=20°–100° C., polymer flow rate=5–200 ml/min., and nozzle diameter= 0.2–4 mm ID. Microparticles ranging in diameter between one and ten microns can be obtained with a morphology which depends on the selection of polymer, concentration, molecular weight and spray flow.

If the imaging agent is a solid, the agent may be encapsulated as solid particles which are added to the polymer solution prior to spraying, or the imaging agent can be dissolved in an aqueous solution which then is emulsified with the polymer solution prior to spraying, or the solid may be cosolubilized together with the polymer in an appropriate solvent prior to spraying.

e. Hydrogel Microparticles. Microparticles made of gel-type polymers, such as polyphosphazene or polymethylmethacrylate, are produced by dissolving the polymer in an aqueous solution, suspending if desired a pore forming agent and suspending a lipid in the mixture, homogenizing the mixture, and extruding the material through a microdroplet forming device, producing microdroplets which fall into a hardening bath consisting of an oppositely charged ion or polyelectrolyte solution, that is slowly stirred. The advantage of these systems is the ability to further modify the surface of the microparticles by coating them with polycationic polymers, like polylysine after fabrication. Microparticle particles are controlled by using various size extruders.

Additives to Facilitate Microparticulate Formation

A variety of surfactants may be added during the synthesis of the image agent-containing microparticles. Exemplary emulsifiers or surfactants which may be used (0.1–5% by weight) include most physiologically acceptable emulsifiers. Examples include natural and synthetic forms of bile salts or bile acids, both conjugated with amino acids and unconjugated such as taurodeoxycholate, and cholic acid.

Pore forming agents can be included in an amount of between 0.01% and 90% weight to volume, to increase pore formation. For example, in spray drying, solvent evaporation, a pore forming agent such as a volatile salt, for example, ammonium bicarbonate, ammonium acetate, ammonium chloride or ammonium benzoate or other lyophilizable salt, is first dissolved in water. The solution containing the pore forming agent is then emulsified with the polymer solution to create droplets of the pore forming agent in the polymer. This emulsion is then spray dried or taken through a solvent evaporation/extraction process. After the polymer is precipitated, the hardened microparticles are frozen and lyophilized to remove the pore forming agents.

Microparticle Size

In a preferred embodiment for the preparation of injectable microparticles capable of passing through the pulmonary capillary bed, the microparticles should have a diameter of between approximately one and ten microns. Larger microparticles may clog the pulmonary bed, and smaller microparticles may not provide sufficient echogenicity. Larger microparticles are useful for administration by routes other than injection, for example oral (for evaluation of the gastrointestinal tract), application to other mucosal surfaces (rectal, vaginal, oral, nasal) or by inhalation. The preferred particle size for oral administration is about 0.5 microns and 5 mm. Useful pharmaceutically acceptable carriers include saline containing glycerol and TWEEN™ 20 and isotonic mannitol containing TWEEN™ 20. Particle size analysis can be performed on a Coulter counter by light microscopy, scanning electron microscopy, or transmittance electron microscopy.

Targeting

The microparticles can be targeted specifically or non-specifically through the selection of the polymer forming the microparticle, the size of the microparticle, and/or incorporation or attachment of a ligand to the microparticles. For example, biologically active molecules, or molecules affecting the charge, lipophilicity or hydrophilicity of the particle, may be attached to the surface of the microparticle. Additionally, molecules may be attached to the microparticles which minimize tissue adhesion, or which facilitate specific targeting of the microparticles in vivo. Representative targeting molecules include antibodies, lectins, and other molecules which are specifically bound by receptors on the surfaces of cells of a particular type.

Inhibition of Uptake by the RES

Uptake and removal of the microparticles can also be minimized through the selection of the polymer and/or incorporation or coupling of molecules which minimize adhesion or uptake. For example, tissue adhesion by the microparticle can be minimized by covalently binding poly (alkylene glycol) moieties to the surface of the microparticle. The surface poly(alkylene glycol) moieties have a high affinity for water that reduces protein adsorption onto the surface of the particle. The recognition and uptake of the microparticle by the reticulo-endothelial system (RES) is therefore reduced.

For example, the terminal hydroxyl group of the poly (alkylene glycol) can be used to covalently attach biologically active molecules, or molecules affecting the charge, lipophilicity or hydrophilicity of the particle, onto the surface of the microparticle. Methods available in the art can be used to attach any of a wide range of ligands to the microparticles to enhance the delivery properties, the stability or other properties of the microparticles in vivo.

Diagnostic Applications

Microparticles are typically combined with a pharmaceutically acceptable carrier such as phosphate buffered saline or saline or mannitol, then an effective amount for detection administered to a patient using an appropriate route, typically by injection into a blood vessel (i.v.) or orally. Microparticles containing an encapsulated imaging agent may be used in vascular imaging, as well as in applications to detect liver and renal diseases, in cardiology applications, in detecting and characterizing tumor masses and tissues, and in measuring peripheral blood velocity. The microparticles also can be linked with ligands that minimize tissue adhesion or that target the microparticles to specific regions of the body in vivo as described above.

The methods and compositions described above will be further understood with reference to the following non-limiting examples.

Example 1

Preparation of Octafluoropropane PEG-PLGA/ PLGA microparticles with Lecithin.

3.2 grams of PEG-PLGA (75:25) (IV=0.75 dL/g Birmingham Polymers), 6.4 g PLGA (50:50) (IV=0.4 dL/g Henley Chemicals), 23 mg Lecithin (Spectrum Chemicals), and 193 mg of Palmitic Acid (Spectrum Chemicals) were dissolved in 190 ml of methylene chloride. 10.8 ml of 0.70 g/ml ammonium acetate was added to the polymer solution and the polymer/ ammonium acetate was added to the polymer solution and the polymer/ammonium acetate mixture was homogenised at 10,000 RPM for 1 minute using a Virtis homogeniser. The solution was pumped at a flowrate of 20 ml/min and sprayed dried using a Bucchi Lab spray dryer. The inlet temperature was 40° C. The microparticle powder was collected and lyophilized on an FTS tray lyophilizer for 120 hours. The microparticles were aliquoted into 5 ml Purform vials and sealed with butyl stoppers and crimped. The vials were filled with octofluoropropane at a pressure of 10 psig and purged continuously under the gas for three minutes. After this point the vials were stored at 4° C. until used. The particle diameters ranged from 1–10 microns when sized on a coulter counter with a number average mean of 2.0 microns. Scanning electron microscopy demonstrated the particles to be generally spherical with smooth surfaces and occasional surface crenulations.

Example 2

Preparation of Octafluoropropane PEG-PLGA/ PLGA microparticles with dipalmitoylphosphatidylcholine (DPPC).

Microparticles were prepared as in Example 1 except 29.6 mg of dipalmitoylphosphatidylcholine (Avanti, Birmingham Ala.) was used in place of the lecithin.

Example 3

Preparation of Octafluoropropane PEG-PLGA/ PLGA microparticles with distearoylphosphatidylcholine (DSPC).

Microparticles were prepared as in Example 2 except that 29.9 mg of distearoylphosphatidylcholine (Avanti, Birmingham Ala.) was used in place of the lecithin.

Example 4

Preparation of Octafluoropropane PEG-PLGA/ PLGA microparticles with diarachidoylphosphatidylcholine (DAPC).

Microparticles were prepared as in Example 2 except that 29.9 mg of diarachidoylphosphatidylcholine (Avanti, Birmingham Ala.) in place of the lecithin.

Example 5

In Vitro Measurement of Microparticle Backscatter.

The backscatter of the different octafluoropropane containing polymeric microparticles produced in Examples 1–4 was obtained by exposing 10 microliters of suspension of the microparticles to a focused ultrasound beam. The backscattered acoustic power as a function of depth into the sample was determined as follows. A pulser-receiver (Panametrics® Model 5800) was used to shock excite a focused ultrasound transducer (2.25 MHz), which sends a pulse of ultrasound into the suspension of microparticles in physiological saline.

The suspension was contained in a cylindrical sample chamber (55 ml of saline) which is situated in a temperature-controlled water bath adjusted to 37° C. The chamber was positioned 1.5 inches from the transducer, such that the transducer was focused on the acoustic window of the chamber. Chambers were rotated at 15 rpm to maintain the microparticles in suspension. The dissolved gas content of the saline was maintained at approximately 90% of air saturation, as determined by a dissolved oxygen meter (Orion® model 840). The operation of the acoustic test system is controlled by a PC running a proprietary program written under LabVIEW® (National Instruments®). The computer triggered the pulser-receiver to shock excite the ultrasound transducer.

The backscattered signal was received by the same transducer, and the returned signal was amplified by the pulser-receiver unit. The amplified signal was passed to a digital oscilloscope (LeCroy® model 9310AM) for digitization at 100 MSa/s. The digitized signal was further processed. The signal was squared, analyzed by FFT and integrated over the 6 dB bandwidth of the transducer. The acoustic data collected by the system was converted to integrated backscattered power (IBP), in arbitrary units, as a function of depth in the microparticulate suspension. The IBP vs depth data from 50 pulses were averaged, the best-fitting straight line through the averaged IBP data determined and the y-intercept which is proportional to the backscatter coefficient was determined. Each sample was tested at 2.5 minute intervals over a total time period of 10 minutes.

Figure 1:
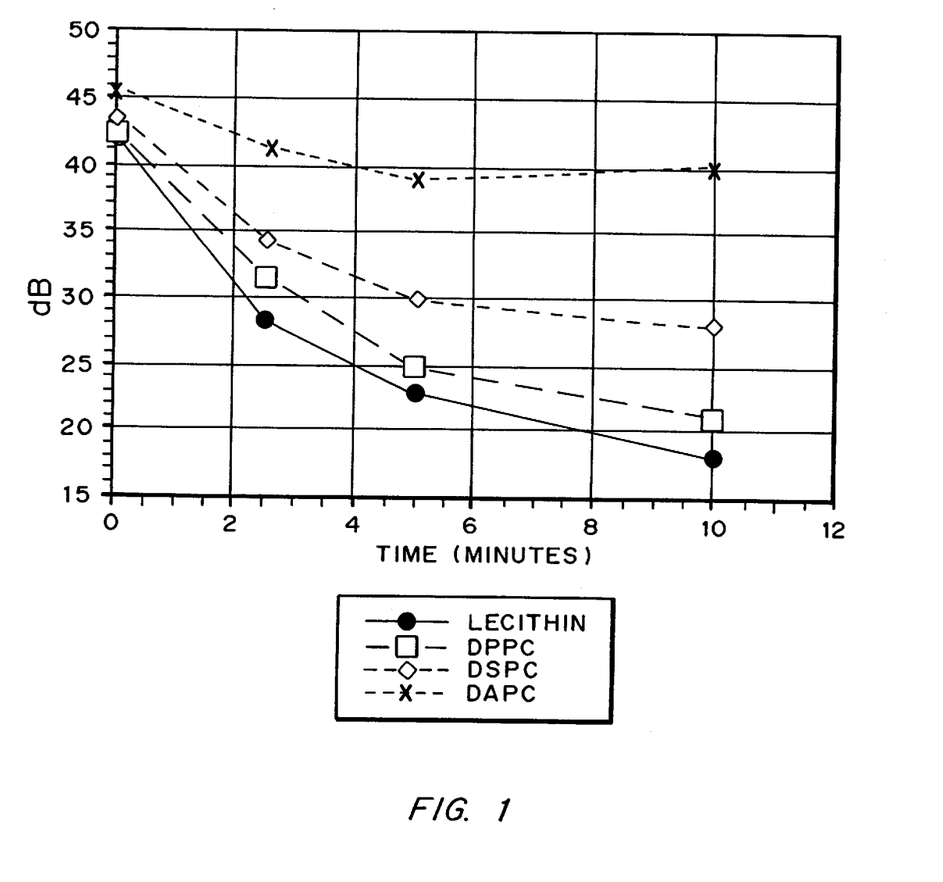
FIG. 1 is a graph of the effect of carbon chain length of lipid incorporated into polymeric microparticles, plotted as degree of backscattering over time (minutes) for lecithin (solid circles), DPPC (open squares), DSPC (open diamonds), and DAPC (X).

The backscatter as a function of time for the four different microparticle lots is shown in FIG. 1. Lecithin is a mixture of different chain length phospholipids. As the chain length of the fatty acid attached to the phosphocholine is increased, the magnitude of backscatter is more sustained over a longer period of time indicating increased stability of the octafluoropropane in the microparticles. Using the highly purified phospholipids is also more effective at stabilization of the gas as compared to the mixture of phospholipids contained in lecithin.

Modifications and variations of the present invention will be obvious to those skilled in the art from the foregoing detailed description and are intended to come within the scope of the following claims.

We claim:

1. A method for making microparticles for diagnostic imaging, wherein the microparticles are formed of a biocompatible polymer and have incorporated therein gas, the improvement comprising (a) incorporating into the polymer a hydrophobic compound by either dissolving the polymer and hydrophobic compound in an organic solvent or melting the polymer with the hydrophobic compound, prior to forming the microparticles, and (b) forming the microparticles by either removing the polymer solvent or cooling the polymer, wherein the hydrophobic compound is mixed with the polymer in the microparticle in an amount effective to increase the echogenicity of the microparticle as compared to the echogenicity of the microparticle without the hydrophobic compound and wherein the hydrophobic compound is selected from the group consisting of fatty acids, fatty acid alcohols, fatty acid anhydrides, hydroxy fatty acids, prostaglandins, phospholipids, sphingolipids, steroids and steroid derivatives, fat soluble vitamins, terpenes, tryptophan, tyrosine, isoleucine, leucine, valine, alkyl paraben, and benzoic acid.

2. The method of claim 1 wherein the hydrophobic compound is incorporated with the polymer at a ratio of between 0.01 and 30 by weight of hydrophobic compound to weight of polymer.

3. The method of claim 2 wherein the hydrophobic compound is a lipid incorporated with the polymer at a ratio of between 0.01 and 30 (weight lipid/weight polymer).

4. The method of claim 1 wherein the lipid is a phospholipid selected from the group consisting of phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and $\beta$-acyl-y-alkyl phospholipids.

5. The method of claim 4, wherein the phospholipid is selected from the group consisting of dioleoylphosphatidylcholine, dimyristoylphosphatidylcholine, dipentadecanoylphosphatidylcholine dilauroylphosphatidylcholine, dipalmitoylphosphatidylcholine, distearoylphosphatidylcholine, diarachidoylphosphatidylcholine, dibehenoylphosphatidylcholine, ditricosanoylphosphatidylcholine, dilignoceroylphatidylcholine; and phosphatidylethanolamines.

6. The method of claim 1 wherein the gas is selected from the group consisting of fluorinated gases, oxygen, xenon, argon, helium, and air.

7. The method of claim 6 wherein the gas is selected from the group consisting of $CF_4$, $C_2F_6$, $C_3F_8$, $C_4F_8$, $C_4F_{10}$, $SF_6$, $C_2F_4$, and $C_3F_6$.

8. The method of claim 7 wherein the gas is octafluoropropane.

9. The method of claim 1 wherein the microparticle is formed of a synthetic polymer.

10. The method of claim 1 wherein the microparticle is formed of a natural polymer.

11. The method of claim 1 wherein the microparticle is formed of a bioadhesive polymer.

12. The method of claim 9 wherein the microparticle is formed of a synthetic polymer selected from the group consisting of poly(hydroxy acids), polyanhydrides, polyorthoesters, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly (valeric acid), and poly(lactide-co-caprolactone), ethylene vinyl acetate, copolymers and blends thereof.

13. A composition for diagnostic imaging comprising biocompatible polymeric microparticles incorporating a gas which are formed by the steps of (a) dissolving the polymer and a hydrophobic compound in an organic solvent or melting the polymer and the hydrophobic compound, prior to forming the microparticles, (b) forming the microparticles by removing the solvent or cooling the polymer, wherein the hydrophobic compound is mixed with the polymer in the microparticle in an amount effective to increase the echogenicity of the microparticle as compared to the echogenicity of the microparticle without the hydrophobic compound, and wherein the hydrophobic compound is selected from the group consisting of fatty acids, fatty acid alcohols, fatty acid anhydrides, hydroxy fatty acids, prostaglandins, phospholipids, sphingolipids, steroids and steroid derivatives, fat soluble vitamins, terpenes, tryptophan, tyrosine, isoleucine, leucine, valine, alkyl paraben, and benzoic acid.

14. The microparticles of claim 13 wherein the hydrophobic compound is incorporated with the polymer at a ratio of between 0.01 and 30 by weight of hydrophobic compound to weight of polymer.

15. The microparticles of claim 14 wherein the hydrophobic compound is a lipid incorporated with the polymer at a ratio of between 0.01 and 30 (weight lipid/weight polymer).

16. The microparticles of claim 13 wherein the lipid is a phospholipid selected from the group consisting of phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and $\beta$-acyl-y-alkyl phospholipids.

17. The microparticles of claim 16 wherein the phospholipid is selected from the group consisting of dioleoylphosphatidylcholine, dimyristoylphosphatidylcholine, dipentadecanoylphosphatidylcholine dilauroylphosphatidylcholine, dipalmitoylphosphatidylcholine, distearoylphosphatidylcholine, diarachidoylphosphatidylcholine, dibehenoylphosphatidylcholine, ditricosanoylphosphatidylcholine, dilignoceroylphatidylcholine; and phosphatidylethanolamines.

18. The microparticles of claim 13 wherein the gas is selected from the group consisting of fluorinated gases, oxygen, xenon, argon, helium, and air.

19. The microparticles of claim 18 wherein the gas is selected from the group consisting of $CF_4$, $C_2F_6$, $C_3F_8$, $C_4F_8$, $C_4F_{10}$, $SF_6$, $C_2F_4$, and $C_3F_6$.

20. The microparticles of claim 19 wherein the gas is octafluoropropane.

21. The microparticles of claim 13 wherein the microparticle is formed of a synthetic polymer.

22. The microparticles of claim 21 wherein the polymer is selected from the group consisting of poly(hydroxy acids), polyanhydrides, polyorthoesters, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly (lactide-co-caprolactone), ethylene vinyl acetate, copolymers and blends thereof.

23. The microparticles of claim 15 wherein the lipid is liquified with the polymer to form the microparticles.

24. The microparticles of claim 23 wherein the lipid and the polymer are dissolved in a solvent for both, then formed into microparticles.

25. The microparticles of claim 23 wherein the gas is incorporated into the microparticle after the polymer and lipid have solidified.

26. The microparticles of claim 13 wherein the polymer is a natural polymer selected from the group consisting of proteins and polysaccharides.

27. In a method for increasing the hydrophobicity of microparticles formed of a biocompatible hydrophobic polymer and having incorporated therein a gaseous imaging agent, the improvement comprising dissolving the polymer and a hydrophobic compound in an organic solvent or melting the polymer and a hydrophobic compound, removing the solvent or cooling the polymer to form the microparticles, wherein the hydrophobic compound is mixed with the polymer in the microparticle in an amount effective to increase the echogenicity of the microparticle as compared to the echogenicity of the microparticle without the hydrophobic compound.

28. The method of claim 27, wherein the hydrophobic compound is selected from the group consisting of fatty acids, fatty acid alcohols, fatty acid anhydrides, hydroxy fatty acids, prostaglandins, phospholipids, sphingolipids, steroids and steroid derivatives, fat soluble vitamins, terpenes, tryptophan, tyrosine, isoleucine, leucine, valine, alkyl paraben, and benzoic acid.

* * * * *